US006441148B1

(12) United States Patent
Radomski et al.

(10) Patent No.: US 6,441,148 B1
(45) Date of Patent: Aug. 27, 2002

(54) METHOD FOR ISOLATION OF XYLANASE GENE SEQUENCES FROM SOIL DNA, COMPOSITIONS USEFUL IN SUCH METHOD AND COMPOSITIONS OBTAINED THEREBY

(75) Inventors: Christopher C. A. Radomski, Abbotsford (CA); Kah Tong Seow, Singapore (SG); R. Antony J. Warren, Vanouver (CA); Wai Ho Yap, Singapore (SG)

(73) Assignee: Terragen Diversity, Inc., Vancouver (CA)

( * ) Notice: Subject to any disclaimer, the term of this patent is extended or adjusted under 35 U.S.C. 154(b) by 0 days.

(21) Appl. No.: 09/130,337

(22) Filed: Aug. 6, 1998

Related U.S. Application Data

(62) Division of application No. 08/716,942, filed on Sep. 20, 1996, now Pat. No. 5,849,491.
(60) Provisional application No. 60/004,157, filed on Sep. 22, 1995.

(51) Int. Cl.$^7$ .............................................. C07H 21/02

(52) U.S. Cl. .................. 536/23.1; 536/24.3; 536/24.33; 536/23.2; 435/6; 435/91.1; 435/91.2; 435/5

(58) Field of Search ..................... 435/6, 91.2, 91.1, 435/5; 536/23.1, 24.3, 24.33, 23.2

(56) References Cited

U.S. PATENT DOCUMENTS

| 5,306,633 A | * | 4/1994 | Gottschalk et al. ......... 435/200 |
| 5,498,534 A | * | 3/1996 | Jeffries et al. .............. 435/278 |
| 5,610,048 A | | 3/1997 | Schulein et al. | |
| 5,849,491 A | | 12/1998 | Radomski et al. | |

FOREIGN PATENT DOCUMENTS

| EP | 0 517 418 | 12/1992 |
| JP | 62-77061 | 10/1994 |
| WO | WO 91/18974 | 12/1991 |
| WO | WO 95/14770 | 6/1995 |
| WO | WO 95/18219 | 7/1995 |
| WO | WO 95/34662 | 12/1995 |

OTHER PUBLICATIONS

O'Neill, "Structure of the gene encoding the exoglucanase of Cellulomonas fimi", Gene, vol. 44, pp. 325–330, 1986.*
O'Neill, Genbank Accession No. L11080, 1986.*
Millward–Sadler, "Novel cellulose–binding domains, NodB homologues and conserved modular architecture in xylanases from the aerobic soil bacteria Pseudomonas fluorescens . . . " Biochem J., 312(pt 1), pp. 39–48, Nov. 1995.*
Kaiser et al. DNA Cloning 1, 1995.*
Scharf, "Cloning with PCR", PCR Protocols, 1990.*
Barns et al., 1994, "Remarkable Archael Diversity Detected in a Yellowstone National Park Hot Spring Environment", Proc. Nat'l Acad. Sci. (USA) 91: 1609–1613.

Bergquist et al., 1994, "Hemicellulolytic Enzymes From Extremely Thermophilic Bacteria—Application of Molecular Genetics to Pulp Bleaching", poster presented at Society for Industrial Microbiology Meeting, Montreal, Canada, Jun. 1994.
Crameri et al., 1996, "Improved Green Fluorescent Protein by Molecular Evolution Using DNA Shuffling", Nature Biotechnology 14: 315–319.
Don et al., 1991, "Touchdown PCR to Circumvent Spurious Priming During Gene Amplification", Nucl. Acids Res. 19:4008.
Herrick et al., 1993, "Polymerase Chain Reaction Amplification of Naphthalene–Catabolic and 16S rRNA Gene Sequences from Indigenous Sediment Bacteria", Appl. and Environmental Microbiol. 59:687–694.
Holben et al., 1988, "DNA Probe Method for the Detection of Specific Microorganisms in the Soil Bacterial Community", Appl. Environ. Microbiol. 54: 703–711.
Johnston and Aust, 1994, "Detection of Phanerochaete chrysosporium in Soil by PCR and Restriction Enzyme Analysis", Applied and Environmental Microbiol. 60: 2350–2354.
Knaebel and Crawford, 1995, "Extraction and Purification of Microbial DNA from Petroleum–Contaminated Soils and Detection of Low Numbers of Toluene, Octane and Pesticide Degraders by Multiplex Polymerase Chain Reaction and Southern Analysis", Molecular Ecology 4:579–591.
Matsumura and Ellington, 1996, "DNA Shuffling Brightens Prospects for GFP", Nature Biotechnology 14:366.
McCubbin, 1994, "A Bleaching Revolution is in Progress", Pulp & Paper Canada 94: 12–16.
Munro et al., 1995, "A Gene Encoding a Thermophilic Alkaline Serine Proteinase from Thermus sp. Strain Rt41A and Its Expression in *Escherichia coli*", Microbiology 141:1731–1738.

(List continued on next page.)

*Primary Examiner*—Lisa B. Arthur
*Assistant Examiner*—Jeanine Goldberg
(74) *Attorney, Agent, or Firm*—Fish & Neave; James F. Haley, Jr.; Karen E. Brown

(57) ABSTRACT

Xylanase DNA is recovered from soil by PCR amplification using degenerate primers. Because of the complexity of the soil samples, it is likely that the recovered product will include more than one species of polynucleotide. These recovered copies may be cloned into a host organism to produce additional copies of each individual species prior to characterization by sequencing. Recovered DNA which is found to vary from known xylanases can be used in several ways to facilitate production of novel xylanases for industrial application. First, the recovered DNA, or probes corresponding to portions thereof, can be used as a probe to screen DNA libraries and recover intact xylanase genes including the unique regions of the recovered DNA. Second, the recovered DNA or polynucleotides corresponding to portions thereof, can be inserted into a known xylanase gene to produce a recombinant xylanase gene with the sequence variations of the recovered DNA.

13 Claims, 2 Drawing Sheets

OTHER PUBLICATIONS

Patil et al., 1990, "PCR Amplification of an *Escherichia coli* Gene Using Mixed Primers Containing Deoxyadensine at Ambiguous Positions in Degenerate Amino Acid Codons", Nucl. Acids Res. 18:3080 [erratum appears at Nucleic Acids Res. 19:3184 (1991)].

Porteous et al., 1994, "An Effective Method to Extract DNA from Environmental Samples for Polymerase Chain Reaction Amplification and DNA Fingerprint Analysis", Curr. Microbiol. 29: 301–307.

Porteous and Armstrong, 1993, "A Simple Mini–Method to Extract DNA Directly from Soil for Use with Polymerase Chain Reaction Amplification", Curr. Microbiol. 27:115–118.

Porteous and Armstrong, 1991, "Recovery of Bulk DNA from Soil by a Rapid, Small–Scale Extraction Method", Current Microbiology 22:345–348.

Recorbet et al., 1993, "Kinetics of the Persistence of Chromosomal DNA from Genetically Engineered *Escherichia coli* Introduced into Soil", Appl. and Environmental Microbiol. 59:4289–4294.

Roux, 1994, "Using Mismatched Primer–Template Pairs in Touchdown PCR", BioTechniques 16: 812–814.

Saddler, 1993, in: *Bioconversion of Forest and Agricultural Plant Residues*, CAB Int'l, Wallingford, England, pp. 1–11.

Smalla et al., 1993, "Rapid DNA Extraction Protocol from Soil for Polymerase Chain Reaction–Mediated Amplification", J. Appl. Bacteriol. 74:78–85.

Steffan et al., 1991, "Polymerase Chain Reaction: Applications in Environmental Microbiology", Annu. Rev. Microbiol. 45:137–161.

Tebbe et al., 1993, "Interference of Humic Acids and DNA Extracted Directly from Soil in Detection and Transformation of Recombinant DNA from Bacteria and a Yeast", Appl. and Environ. Microbiol. 59:2657–2665.

Tiedje, 1994, "Microbial Diversity: Of Value to Whom?", ASM News 60:524–525.

Wick, 1994, "Enzymology Advances Offer Economical and Environmentally Safe Ways to Make Paper", Genetic Engineering News 14:1.

* cited by examiner

Fig. 2

```
                           SEQUENCE LISTING

<160> NUMBER OF SEQ ID NOS: 25

<210> SEQ ID NO 1
<211> LENGTH: 21
<212> TYPE: DNA
<213> ORGANISM: Artificial sequence
<220> FEATURE:
<221> NAME/KEY: SITE
<222> LOCATION: (13) ... (13)
<223> OTHER INFORMATION: n = inosine
<221> NAME/KEY: SITE
<222> LOCATION: (16) ... (16)
<223> OTHER INFORMATION: n = inosine
<223> OTHER INFORMATION: Description of Artificial sequence: primer

<400> SEQUENCE: 1
cgsggscaca csntsntstg g                                              21

<210> SEQ ID NO 2
<211> LENGTH: 20
<212> TYPE: DNA
<213> ORGANISM: Artificial sequence
<220> FEATURE:
<223> OTHER INFORMATION: Description of Artificial sequence: Primer
<221> NAME/KEY: SITE
<222> LOCATION: (15) ... (15)
<223> OTHER INFORMATION: n = inosine
<221> NAME/KEY: SITE
<222> LOCATION: (17) ... (17)
<223> OTHER INFORMATION: n = inosine

<400> SEQUENCE: 2
gttgtagtcg ttgwngnasa                                                20

<210> SEQ ID NO 3
<211> LENGTH: 269
<212> TYPE: DNA
<213> ORGANISM: Unknown organism
<220> FEATURE:
<223> OTHER INFORMATION: Description of unknown organism:  soil microbe

<400> SEQUENCE: 3
ggggccacac ggtcgtgtgg gcggtggacg actttgtgca gtcatggatc aaaaaccttt      60
ccaacgggga cctgcggatc catttgacca accgcatcga aagcgtagtc attcatttca    120
cgggcacctt catgcatcgg gatgtgaaca acgaaatgtt gcacggcaat tactacggca    180
accgcctcgg cgattccatc aactcctgga tgttcaaaca cgcccgcttg caggacagca    240
acgtcgtgct ctccctcaac gactacaac                                      269

<210> SEQ ID NO 4
```

```
<211> LENGTH: 288
<212> TYPE: DNA
<213> ORGANISM: Unknown organism
<220> FEATURE:
<223> OTHER INFORMATION: Description of unknown organism: soil microbe

<400> SEQUENCE: 4
cgcgggcaca ccgtcgtgtg gcacaaccag cttcccgggt gggtgacggc gacggccgcg      60
agcagcgacg agcaggccgc ggtgctgcag gcgcacgtca ctcaggaggt cgaccacttc     120
cgcggccaca tctacgcgtg ggacgtcgtc aacgagccgt tcaacgatga cggcacctgg     180
cgcgacacca tctggtaccg ccccatgggt ccggactaca tcgcgcaggc cttccgctgg     240
gtccgcgcgg cggacctaga tgcccggctg tcccacaacg actacaac                  288

<210> SEQ ID NO 5
<211> LENGTH: 288
<212> TYPE: DNA
<213> ORGANISM: Unknown organism
<220> FEATURE:
<223> OTHER INFORMATION: Description of unknown organism: soil microbe

<400> SEQUENCE: 5
cgggggcaca cggtggtgtg gcacaaccag cttcccgggt gggtgacggc gacggccgcg      60
agcagcgacg agcaggccgc ggtgctgcag gcgcacgtca ctcaggaggt cgaccacttc     120
cgcggccaca tctacgcgtg ggacgtcgtc aacgagccgt tcaacgatga cggcacctgg     180
cgcgacacca tctggtaccg cgccatgggt ccggactaca tcgcgcaggc cttccgctgg     240
gctcgcgcgg cggacctaga tgcccggctg tccctcaacg actacaac                  288

<210> SEQ ID NO 6
<211> LENGTH: 288
<212> TYPE: DNA
<213> ORGANISM: Unknown organism
<220> FEATURE:
<223> OTHER INFORMATION: Description of unknown organism: soil microbe

<400> SEQUENCE: 6
cgtgggcaca ccgtcgtgtg gcacaaccag ctgcccggct gggtcaccac cggtgccttc      60
agcagcgacg agctcgccgt catcctgcag cagcacatca ccgagaaggt cggacacttc     120
gccgggcaca tctccgtgtg ggacgtggtc atcgagccgc tcaacgacga tggcacctgg     180
cgcgacacca tctggtaccg cgctctgggt ccgggttacg tcacgcaggc gttgcgctgg     240
gcgcacgcgg ctgaccccgg cgccaggctg tccctcaacg actacaac                  288

<210> SEQ ID NO 7
<211> LENGTH: 269
<212> TYPE: DNA
<213> ORGANISM: Unknown organism
<220> FEATURE:
<223> OTHER INFORMATION: Description of unknown organism: soil microbe

<400> SEQUENCE: 7
ggcacaacca gttgccagcc tggctcacaa gcggtgcatt cagcagcgcc gagctggcca      60
ccatcctgga gcagcacgtc acccaggaag cggaccattt ccgcgggcac atctacgcct     120
gggacatcgt caacgagccg ttcaacgacg atggcacctg gcgtgacagc ctctggtacc     180
gcgcgctggg cgccggctac gtcgcccagg cgttgcgctg gccccgcgcg gccgatccgt     240
ctgcccggtt ctccctcaac gactacaac                                       269
```

<210> SEQ ID NO 8
<211> LENGTH: 282
<212> TYPE: DNA
<213> ORGANISM: Unknown organism
<220> FEATURE:
<223> OTHER INFORMATION: Description of unknown organism: soil microbe

<400> SEQUENCE: 8

```
cgcgggcaca ccgtcgtctg gcactcgcaa ctgccgtcgt gggtcagtaa tcttccgacc      60
aaccaggtgc agtcggtgat ggaagcccac atcacgaccg aggccaccca ctacaagggg    120
aaggtctacg cctgggacgt cgtcaatgaa ccgtccaacg acgacggtac gctgcgccag    180
gaggttttct atcgtgccat gggcaccggc tacatcgccg acgcgatccg taccgcccac    240
accgccgacc ccaccgccaa gctctcccac aacgactaca ac                       282
```

<210> SEQ ID NO 9
<211> LENGTH: 282
<212> TYPE: DNA
<213> ORGANISM: Unknown organism
<220> FEATURE:
<223> OTHER INFORMATION: Description of unknown organism: soil microbe

<400> SEQUENCE: 9

```
cgggggcaca cggtcgtctg gcactcgcaa ctgccgtcgt gggtcagtaa tctcccgacc      60
aaccaggtgc agtcggtgat ggaagcccac atcacgaccg aggccaccca ctacaagggg    120
aaggtctacg cctgagacgt cgtcaatgaa ccgttcaacg acgacggtac gctgcgccag    180
gacgttttct atcgtgccat gggcaccggc tacatcgccg acgcgatccg taccgcccac    240
accgccgacc ccaccgccaa gctctccctc aacgactaca ac                       282
```

<210> SEQ ID NO 10
<211> LENGTH: 288
<212> TYPE: DNA
<213> ORGANISM: Unknown organism
<220> FEATURE:
<223> OTHER INFORMATION: Description of unknown organism: soil microbe

<400> SEQUENCE: 10

```
cgggggcaca ccgtcgtgtg gcactcgcag ctctccacct ggctgacgtc gggcacgtgg      60
accgccgcgc aggcgacgac gctgatgacg gaccacatcg ccaacgtcgt cggccactac    120
aagggcagc tcgtcgcgtg ggacgtggtc aacgaagcgc tgaacgacga tggcacgtat    180
cggtcgggt tctactacga ccacatcggc ccgacgtaca tcgagacggc gttccgcgcg    240
gcgcacaccg ccgactcgac ggtgctgctg tcccacaacg actacaac                 288
```

<210> SEQ ID NO 11
<211> LENGTH: 291
<212> TYPE: DNA
<213> ORGANISM: Unknown organism
<220> FEATURE:
<223> OTHER INFORMATION: Description of unknown organism: soil microbe

<400> SEQUENCE: 11

```
cgcgggcaca ccgtcgtctg gcacgaccag ctctccacct gggtgacgac gggcaattac      60
agcgctgccc aagcggactc cattctcgta tcgtacatca ccactgtgat gacgcgatac    120
aagggtaagg tcgggatctg ggatgtcgtc aatgaagcca tgggcgatga tgcagtgatc    180
cgcacctcgt cctattggta tcagaagctc ggaccgaact acatcgagcg cgcatttcgt    240
ctcgccaaca gcgttgatcc gacggcaaag ctgtccctca acgactacaa c             291
```

<210> SEQ ID NO 12
<211> LENGTH: 298
<212> TYPE: DNA
<213> ORGANISM: Unknown organism
<220> FEATURE:
<223> OTHER INFORMATION: Description of unknown organism: soil microbe

<400> SEQUENCE: 12

```
gggccacacg gtggtctggc ataaccagac gcccaagtgg gtcttcgaag acgacaaggg    60
tcaacccctc actcgcgacg ccctcctcgt ccgtctcaaa gagcacatta ataaggtagt   120
cggccgctac aaaggccgta tcaacggttg ggacgtcgtc aacgaggcca tcaacgaaga   180
cggcaccatg cgccagtcgc cctggatgaa gatcatcggc gacgacttca tcgaactcgc   240
attccagtac gcgcacgacg ccgacccgca agccgagctc tcccacaacg actacaac    298
```

<210> SEQ ID NO 13
<211> LENGTH: 282
<212> TYPE: DNA
<213> ORGANISM: Unknown organism
<220> FEATURE:
<223> OTHER INFORMATION: Description of unknown organism: soil microbe

<400> SEQUENCE: 13

```
gggcacaccg tggtctggca ctcgcaacag ccaggctgga tgcagagcct gagcggcacc    60
gccctgcgca acgccatgat caaccatatc aacggcgtga tggcccacta taaggcaag   120
ctcgcctact gggatgtggt caacgaagcc ttcgcggacg acggcagcca gaaccgccgc   180
aactcgaacc tccagcagac cggcaacgac tggatcgagg tcgccttcaa gacggctcgc   240
gccgccgatg gctcggtcaa gctctcccac aacgactaca ac                      282
```

<210> SEQ ID NO 14
<211> LENGTH: 311
<212> TYPE: DNA
<213> ORGANISM: Unknown organism
<220> FEATURE:
<223> OTHER INFORMATION: Description of unknown organism: soil microbe

<400> SEQUENCE: 14

```
gccacacggt ggtctggcat tcgcagacgg gcggctggtt cttccagggc gccgatggtc    60
agccggcgac gcgcgaagta gtgatggagc ggctccataa gcacatcacg acggtcgtcg   120
gccgctacaa aggaaaggtc cttgggtggg acgtcgtcaa tgagtcgatc aacgacaatg   180
gcgacggcac gacggaaaac ctgcggacga gcagttggta tcgtgcgatc gggccggatg   240
tgctgacgat ggcgttcaag tgggcgcatg aagcggatcc ggatgcgctg ctctcccctca   300
acgactacaa c                                                         311
```

<210> SEQ ID NO 15
<211> LENGTH: 300
<212> TYPE: DNA
<213> ORGANISM: Unknown organism
<220> FEATURE:
<223> OTHER INFORMATION: Description of unknown organism: soil microbe

<400> SEQUENCE: 15

```
cggggcaca cggtggtctg gcataaccag acgcccaagt gggtcttcga agacgacaag    60
ggtcaacccc tcactcgcga cgccctcctc gtccgtctca agagcacat taataaggta   120
gtcggccgct acaaaggccg tatcaacggt tgggacgtcg tcaacgaagc catcaacgaa   180
gacggcacca tgcgccagtc gccctggatg aagatcatcg gcgacgactt catcgaactc   240
```

```
gcattccagt acgcgcacga cgccgacccg caagccgagc tctcccacaa cgactacaac    300
```

<210> SEQ ID NO 16
<211> LENGTH: 288
<212> TYPE: DNA
<213> ORGANISM: Unknown organism
<220> FEATURE:
<223> OTHER INFORMATION: Description of unknown organism:  soil microbe

<400> SEQUENCE: 16

```
cggggccaca ccgtcgtctg gcagaaccag ctgccggact ggctgaccac cggcacctac     60
acgtcggcac agctgcgaga cctgttgcac aggcacatca ccgacgaggt ctcgcacttc    120
aagggtcaca tctggcagtg ggatgtcgtc aacgaggcgt caacgacga cggcacgatg    180 cgggacaccc tctggctgcg cgccatgggc cctgggtatg ttgccgacgc gttccgctgg    240
gctcaccagg cagatccggg tgccctgctc tccctcaacg actacaac                288
```

<210> SEQ ID NO 17
<211> LENGTH: 288
<212> TYPE: DNA
<213> ORGANISM: Unknown organism
<220> FEATURE:
<223> OTHER INFORMATION: Description of unknown organism:  soil microbe

<400> SEQUENCE: 17

```
cgcgggcaca cggtggtgtg gcatcagtgt gtgccggatt ggttagcgaa tggaaatttc     60
actcgcgatg aggcaatcga actgttgcac aatcatatct cgaccgtgat gggacactac    120 aagggggcgca tccttgactg ggatgtggtc aatgaagcga ttgctgatag tactctgctg    180
cgcgatacgc cctggcgaaa attcatcggc gacgactata ttgaaatggc ctttcgcttc    240
gcccacgaag ccgatccaga tgcgctcctc tccctcaacg actacaac                288
```

<210> SEQ ID NO 18
<211> LENGTH: 282
<212> TYPE: DNA
<213> ORGANISM: Unknown organism
<220> FEATURE:
<223> OTHER INFORMATION: Description of unknown organism:  soil microbe

<400> SEQUENCE: 18

```
cgggggcaca ccgtggtgtg gcacaagcaa ctgggcggct gggtcgaaca actggacgcg     60
cccgcgttgc gagccgcgct cgagcaccac attcgaaccg tcgtggggca ctacaagggg    120
aaactcctgg cctgggacgt cgtcaacgag gccctgggcg acgacggcag ccctcgcaag    180
acggtcttcc tggaaaagct gggtcccgga tacatcgccg atgcgttccg ctgggcgcat    240
gaggccgatc cccaggctct gttgtccctc aacgactaca ac                       282
```

<210> SEQ ID NO 19
<211> LENGTH: 300
<212> TYPE: DNA
<213> ORGANISM: Unknown organism
<220> FEATURE:
<223> OTHER INFORMATION: Description of unknown organism:  soil microbe

<400> SEQUENCE: 19

```
cgggggcaca cggtggtctg gcataaccag acgcccaagt gggtcttcga agacgacaag     60
ggtcaacccc tcactcgcga cgccctcctc gtccgtctca aagagcacat taataaggta    120
gtcggccgct acaaaggccg tatcaacggt tgggacgtcg tcaacgaagc catcaacgaa    180
```

```
gacggcacca tgcgccagtc gctctggatg aagatcatcg gcgacgactt catcgaactc    240
gcattccagt acgcgcacga cgccgacccg caagccgagc tctcccacaa cgactacaac    300
```

<210> SEQ ID NO 20
<211> LENGTH: 296
<212> TYPE: DNA
<213> ORGANISM: Unknown organism
<220> FEATURE:
<223> OTHER INFORMATION: Description of unknown organism: soil microbe

<400> SEQUENCE: 20

```
gggggcacac ggtggtgtgg catcaacaga acccagcgtg gttaacgggc actacgtgga     60
acgttgacac actcaagcta ctgctcaagg aacacgttga cagcgtggtc gggcatttca    120
agggcaagat tgccgcgtgg gatgtcgtaa acgaagcgtt caacgatggc acgggtacac    180
ttcgaacaac ggattctccg tgggccacaa ccattgggcg ttcgtacgtt gaactcgcgt    240
tcagagaagc acgcgccatc gatccggccg cgcagctgtc ccacaacgac tacaac       296
```

<210> SEQ ID NO 21
<211> LENGTH: 282
<212> TYPE: DNA
<213> ORGANISM: Unknown organism
<220> FEATURE:
<223> OTHER INFORMATION: Description of unknown organism: soil microbe

<400> SEQUENCE: 21

```
cggggccaca cggtggtctg gcagaaccag ctaccgtcct gggtgtccag cctgccgctg     60
aaccaggtgc agcaggcgat ggaaagccac atcaccacgg aggccagcca ctacaagggc    120
caggtttacg cctgggacgt cgtcaacgag ccgttcaacg gcgacggcag cttcgtcagc    180
gatgtgtttt accgtgcgat gggcagcggg tacatcgccg acgcgctgcg caccgcgcac    240
gccgccgacc ccggcgctca gctgtccctc aacgactaca ac                       282
```

<210> SEQ ID NO 22
<211> LENGTH: 294
<212> TYPE: DNA
<213> ORGANISM: Unknown organism
<220> FEATURE:
<223> OTHER INFORMATION: Description of unknown organism: soil microbe

<400> SEQUENCE: 22

```
cgggggcaca ccgtggtgtg gtacgcgcag aagccggcgt cgttcgagcg cctggtcagc     60
gacgccggcg cgtttcgcga cgcctacgcc gcctacatca cggccgtcgt tggccgctac    120
aggggccgca tcgccggctg gggcgtcgtc aacgagcagg tgaccgacga cggcgccgcg    180
tggcgggaca gcctctggag ccacgcgctc ggaccgctgg aacacatgcg cttcgcctat    240
gaactggccc acgccgccga ccccgcggcc gacctgtccc tcaacgacta caac          294
```

<210> SEQ ID NO 23
<211> LENGTH: 285
<212> TYPE: DNA
<213> ORGANISM: C. fimi

<400> SEQUENCE: 23

```
tacggccaca cgctcgtatg gcactcgcag ctgcccgact gggcgaagaa cctcaacggc     60
tccgcgttcg agagcgcgat ggtcaaccac gtgacgaagg tcgccgacca cttcgagggc    120
aaggtcgcgt cgtgggacgt cgtcaacgag gcgttcgccg acgcggcgg ccgccggcag    180 gactcggcgt ccagcagaa gctcggcaac ggctacatcg agaccgcgtt ccgggcggca    240
```

-continued cgtgcggcgg acccgaccgc caagctgtgc atcaacgact acaac                285

<210> SEQ ID NO 24
<211> LENGTH: 1524
<212> TYPE: DNA
<213> ORGANISM: Unknown organism
<220> FEATURE:
<223> OTHER INFORMATION: Description of unknown organism: soil microbe
<221> NAME/KEY: CDS
<222> LOCATION: (1)...(1524)

<400> SEQUENCE: 24

| | |
|---|---|
| atg acc gtg aga tca atc cag aag agg ctt cgc gta tcg cgg cgc ggc | 48 |
| ggt ggc gcc cgc gcc ggc cgg cca cgt caa cag gtg ctg aca gcg gtg | 96 |
| gcg gcg act gcc tgc gtc gcg ggc ggc gcg ctc gcc gcg gca gtg ctg | 144 |
| gcc gcg gcc ggg ccg gcc acg gcg gcc ggc agc acg ctg cgg gcg gcg | 192 |
| gct gag gcg cag ggc aag tac ttc ggg act gag gtc acc ggg aac atg | 240 |
| atc aac aac tcg acg atc acg aac ctg gca ggc cag cag ttc gac atg | 288 |
| gtc acc ccg ggc aac gag atg aag tgg gac acc acc gag ccg tcc aac | 336 |
| ggg tcc tac aac ttc ggc ccg ggc gac gcg gtc gtg tcg ttc gcc aag | 384 |
| gcg cac ggc atg cgg gtg cgc ggg cac aac ctg gtc tgg cag aac cag | 432 |
| ctc ccg tcg tgg gtt tcc agc ctg ccg ctg aac cag gtg cag cag gcg | 480 |
| atg gaa agc cat gtc acc acg gag gcc agc cac tac aag ggc cag gtt | 528 |
| tac gcc tgg gac gtc gtc aac gag ccg ttc aac ggc gac ggc agc ttc | 576 |
| gtc agc gac gtg ttt tac cgc gcg atg ggc agc ggg tac atc gcc gac | 624 |
| gcg ctg cgc acc gcg cac gcc gcc gac ccc agt gcc cag ctg tac atc | 672 |
| aac gac tac agc atc gag ggc gag aac gcc aag agc aac gcc atg tac | 720 |
| agc ctg gtg cag tcc ctg ctg gcg cag ggg gtg ccg atc aac ggc gtg | 768 |
| ggc ttt gaa agc cac tac atc gtg ggg cag gtg ccc tcg tcg ctg ctg | 816 |
| gcc aac atg cag cgg ttc gct gcc ctg ggc gtc aac gtg gcg gtc acc | 864 |
| gag ctt gac gac cgc gtc cag ctg ccg gcc agc acc gcg agc ctg aac | 912 |
| cag cag gcc acc gac tac gcc acc gtg gtg cgc gac tgc ctg cag gtc | 960 |
| tcc cgc tgc gtc ggc gtg tcg caa tgg ggc gtc ggc gac gcc gac tcc | 1008 |
| tgg atc ccg gga acg ttc ccc ggc tgg ggc gcg gcg acc atg tac gac | 1056 |
| cag aac tac cag ccc aag ccc gcg tac tcc gcc acc ttg tcc gcc ctc | 1104 |
| ggc ggc tcc ggc agc acc ggc ggt ggc agc ggc gag atc cac gcg gtc | 1152 |
| ggg gcg ggc aag tgc ctg gac gtg ccc ggc ctc gcc acc acc gcg ggc | 1200 |
| acc cag ctg gac atc tgg acc tgc aac ggc ggc acc aac cag atc tgg | 1248 |
| acg cac acc tcc gcc aac cag ctg acc gtc tac agc ggc agc agc cag | 1296 |
| atg tgc ctg gac gct tac aac aac cag acc acc ccc ggc acc aag gtg | 1344 |
| gac atc tgg acg tgc aac ggc ggc gct aac cag cag tgg cac gtc aac | 1392 |
| tcc aac ggc acg atc acc agt gcc cag tcc ggg ctg tgc ctg gac gtg | 1440 |
| acc ggc gcc agc acc gcc aac ggc gcg ctg gcc gag ctg tgg acc tgc | 1488 |
| aac agc cag tcc aac cag caa tgg acc ctc gga tga | 1524 |

```
<210> SEQ ID NO 25
<211> LENGTH: 507
<212> TYPE: PRT
<213> ORGANISM: Unknown organism
<220> FEATURE:
<223> OTHER INFORMATION: Description of unknown organism: soil microbe

<400> SEQUENCE: 25

Met Thr Val Arg Ser Ile Gln Lys Arg Leu Arg Val Ser Arg Arg Gly
 1               5                  10                  15

Gly Gly Ala Arg Ala Gly Arg Pro Arg Gln Gln Val Leu Thr Ala Val
            20                  25                  30

Ala Ala Thr Ala Cys Val Ala Gly Ala Leu Ala Ala Ala Val Leu
        35                  40                  45

Ala Ala Ala Gly Pro Ala Thr Ala Ala Gly Ser Thr Leu Arg Ala Ala
    50                  55                  60

Ala Glu Ala Gln Gly Lys Tyr Phe Gly Thr Glu Val Thr Gly Asn Met
65                  70                  75                  80

Ile Asn Asn Ser Thr Ile Thr Asn Leu Ala Gly Gln Gln Phe Asp Met
                85                  90                  95

Val Thr Pro Gly Asn Glu Met Lys Trp Asp Thr Thr Glu Pro Ser Asn
            100                 105                 110

Gly Ser Tyr Asn Phe Gly Pro Gly Asp Ala Val Val Ser Phe Ala Lys
        115                 120                 125

Ala His Gly Met Arg Val Arg Gly His Asn Leu Val Trp Gln Asn Gln
    130                 135                 140

Leu Pro Ser Trp Val Ser Ser Leu Pro Leu Asn Gln Val Gln Gln Ala
145                 150                 155                 160

Met Glu Ser His Val Thr Thr Glu Ala Ser His Tyr Lys Gly Gln Val
                165                 170                 175

Tyr Ala Trp Asp Val Val Asn Glu Pro Phe Asn Gly Asp Gly Ser Phe
            180                 185                 190

Val Ser Asp Val Phe Tyr Arg Ala Met Gly Ser Gly Tyr Ile Ala Asp
        195                 200                 205

Ala Leu Arg Thr Ala His Ala Ala Asp Pro Ser Ala Gln Leu Tyr Ile
    210                 215                 220

Asn Asp Tyr Ser Ile Glu Gly Glu Asn Ala Lys Ser Asn Ala Met Tyr
225                 230                 235                 240

Ser Leu Val Gln Ser Leu Leu Ala Gln Gly Val Pro Ile Asn Gly Val
                245                 250                 255

Gly Phe Glu Ser His Tyr Ile Val Gly Gln Val Pro Ser Ser Leu Leu
            260                 265                 270

Ala Asn Met Gln Arg Phe Ala Ala Leu Gly Val Asn Val Ala Val Thr
        275                 280                 285

Glu Leu Asp Asp Arg Val Gln Leu Pro Ala Ser Thr Ala Ser Leu Asn
    290                 295                 300

Gln Gln Ala Thr Asp Tyr Ala Thr Val Val Arg Asp Cys Leu Gln Val
305                 310                 315                 320

Ser Arg Cys Val Gly Val Ser Gln Trp Gly Val Gly Asp Ala Asp Ser
                325                 330                 335

Trp Ile Pro Gly Thr Phe Pro Gly Trp Gly Ala Ala Thr Met Tyr Asp
            340                 345                 350

Gln Asn Tyr Gln Pro Lys Pro Ala Tyr Ser Ala Thr Leu Ser Ala Leu
```

-continued

```
                    355                 360                 365
Gly Gly Ser Gly Ser Thr Gly Gly Gly Ser Gly Glu Ile His Ala Val
        370                 375                 380

Gly Ala Gly Lys Cys Leu Asp Val Pro Gly Leu Ala Thr Thr Ala Gly
385                 390                 395                 400

Thr Gln Leu Asp Ile Trp Thr Cys Asn Gly Gly Thr Asn Gln Ile Trp
                405                 410                 415

Thr His Thr Ser Ala Asn Gln Leu Thr Val Tyr Ser Gly Ser Ser Gln
                420                 425                 430

Met Cys Leu Asp Ala Tyr Asn Asn Gln Thr Thr Pro Gly Thr Lys Val
            435                 440                 445

Asp Ile Trp Thr Cys Asn Gly Gly Ala Asn Gln Gln Trp His Val Asn
        450                 455                 460

Ser Asn Gly Thr Ile Thr Ser Ala Gln Ser Gly Leu Cys Leu Asp Val
465                 470                 475                 480

Thr Gly Ala Ser Thr Ala Asn Gly Ala Leu Ala Glu Leu Trp Thr Cys
                485                 490                 495

Asn Ser Gln Ser Asn Gln Gln Trp Thr Leu Gly
                500                 505
```

METHOD FOR ISOLATION OF XYLANASE GENE SEQUENCES FROM SOIL DNA, COMPOSITIONS USEFUL IN SUCH METHOD AND COMPOSITIONS OBTAINED THEREBY

This application claims priority to U.S. application Ser. No. 08/716,942, filed on Sep. 20, 1996 and U.S. Provisional Application No. 60/004,157, filed Sep. 22, 1995, now U.S. Pat. No. 5,249,491, the contents of both of which are incorporated herein by reference in their entirety.

FIELD OF THE INVENTION

This application relates to the use of PCR amplification to isolate novel xylanase genes from soil DNA, and to primers useful in such methods and the products obtained thereby.

BACKGROUND OF THE INVENTION

The hydrolysis of cellulose, and hemicellulose, with xylans being a major component of hemicellulose, requires a variety of enzymes having activity as endoglucanases, exoglucanases, and xylanases to work in concert. It is with these systems of enzymes, composed of enzymes from the different cellulase families, that plant material is degraded in nature.

Cellulases have been classified into 12 families (designated A to L), and a single organism may have a set of enzymes with members drawn from several families. Of these families, families F and G show xylanase activity.

There has been an increasing awareness of the potential industrial uses for cellulases and xylanases; examples include biomass conversion, Saddler, J. N., *Bioconversion of forest and agricultural plant residues,* CAN International, Oxford, England (1993), and the role cellulases and xylanases are playing in pulp processing and paper production. Wick, C. B., *Genetic Engineering news* 14: 10–11 (1994). For example, xylanases can be used to make pulp bleaching more environmentally friendly by reducing organochlorine discharges. McCubbin, N., *Pulp & Paper Canada,* 95: 4 (1994).

In identifying and characterizing cellulases and xylanases suitable for use in industry, traditional methods of isolation and selection of cellulase and xylanase-producing organisms continues to be carried out by growth on cellulose and cellulose-like substrates. However, the traditional methods are only suitable for culturable organisms. Considering that it is estimated that only 1% of the organisms present in soil are culturable, Tiedje, J. M., *ASM News* 60:524–525 (1994), these traditional methods only skim the surface of the resource of enzymes which soil could theoretically provide.

Bergquist et al., in a paper delivered at the Society for Industrial Microbiology Meeting in Montreal, Canada in June 1994 discussed methods for isolating hemicellulolytic enzymes from the extremely thermophilic bacteria in hot pools having temperatures as high as 95° C. For non-culturable organisms, they suggest that the polymerase chain reaction (PCR) on total DNA isolated from concentrated hot springs water with primers hybridizing to conserved regions of the known xylanase genes can be used to isolate xylanase DNA. Bergquist did not disclose or suggest methods for recovery of xylanase DNA from far more complex and challenging soil samples.

It is an object of the present invention to provide access to the cellulase and xylanase enzymes produced by non-culturable organisms by providing a mechanism for extracting DNA specific to Family F xylanases from soil.

It is a further object of this invention to provide specific compositions, particularly primers, useful in performing this isolation procedure.

It is still a further object of the invention to provide novel xylanase enzymes containing active sites which have been isolated from soil using the procedures of the present invention.

SUMMARY OF THE INVENTION

The present invention provides a method for recovering xylanase-encoding DNA from soil, comprising the steps of:

(a) treating a soil sample to render DNA in the soil accessible for hybridization with oligonucleotide primers;

(b) combining the treated soil sample with first and second primers in an amplification reaction mixture, said first and second primers hybridizing with conserved regions of the sense and antisense strands respectively of a gene encoding a xylanase and flanking a region of interest in the gene;

(c) thermally cycling the amplification reaction mixture through a plurality of cycles each including at least a denaturation phase and a primer extension phase to produce multiple copies of the region of interest flanked by the primers; and (d) recovering the copies of the region of interest from the amplification reaction mixture. Because of the complexity of the soil samples, it is likely that the recovered product will include more than one species of polynucleotide. Thus, these recovered copies may, in accordance with the invention, be cloned into a host organism to produce additional copies of each individual species prior to characterization by sequencing.

Recovered DNA which is found to vary from known xylanases can be used in several ways to facilitate production of novel xylanases for industrial application. First, the recovered DNA, or probes corresponding to portions thereof, can be used as a probe to screen soil DNA libraries and recover intact xylanase genes including the unique regions of the recovered DNA. Second, the recovered DNA or polynucleotides corresponding to portions thereof, can be inserted into a known xylanase gene to produce a recombinant xylanase gene with the sequence variations of the recovered DNA.

BRIEF DESCRIPTION OF THE DRAWINGS

FIG. 2 shows the sequence differences between twenty DNA fragments isolated using the method of the invention and the sequence of the corresponding region of the Family F xylanase from *Cellulomonas fimi.*

DETAILED DESCRIPTION OF THE INVENTION

Figure 1:
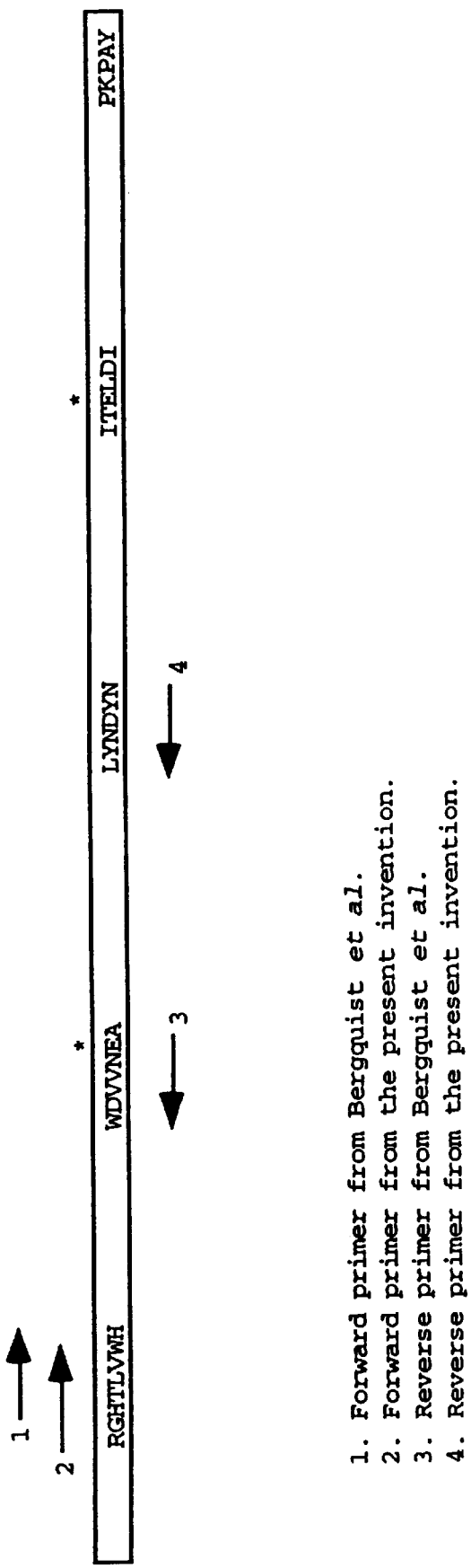
FIG. 1 shows a map of a Family F xylanase gene showing the location of conserved regions suitable for use as primers.

Although the method of the invention for recovering xylanase DNA from soil samples appears in retrospect to be similar to PCR amplification of DNA from other sources (including the hot spring water of Bergquist et al.), the utility of PCR amplification in this environment and for this purpose could no be predicted with any confidence because of the complexity of soil. Soil is a complex mixture of minerals, decaying organic matter, and numerous organisms and microorganisms. As such it contains many possible sources of DNA, and many complex organic materials, e.g., humic materials, which could interfere with primer binding or polymerase enzyme activity to make PCR amplification unworkable. Thus, the very first question addressed in the development of the present invention was whether or not PCR amplification could be performed directly on a soil sample.

To determine whether PCR could be effectively used to amplify Family F cellulase gene fragments in the presence of humic substances carried over into extracted soil samples, soil DNA prepared by direct lysis as described in Barns, et al., *Proc. Natl. Acad. Sci.* 91: 1609–1613 (1994), was spiked with *Cellulomonas fimi* genomic DNA, and PCR was performed using degenerate primers hybridizing to conserved regions of Family F xylanase genes (FIG. 1) and processed in two rounds of PCR, for a total of 70 cycles. Agarose gel electrophoresis was used to separate the PCR products. Evaluation of these gels clearly showed two bands corresponding to about 300 and 400 base pairs for the spiked samples and for an undiluted genomic control. The lower band is the expected size (285 bp) from *C. fimi* genomic DNA. The 400 bp band upon further investigation yielded a putative second family F cellulase member enzyme for *C. fimi*. With increasing dilution of the genomic DNA, more distinct PCR products appear in the regions outside of the 400 bp and 300 bp regions. Overall, these results indicate that the humic substances are not appreciably inhibiting the PCR, and PCR products could be obtained without optimization. In addition, at greater dilutions of the genomic DNA, the target sequences in the soil DNA experience less competition from the genomic DNA for primer binding. This leads to amplification of soil DNA targets.

Since the preliminary experiments showed that PCR could be used to amplify soil DNA, PCR was performed on unspiked soil DNA. In this case, PCR amplification resulted in the amplification of five bands greater than 300 bp. This result is not unexpected as the size of the fragments of family F cellulases that the constructed primers target, in known family F members, are quite heterogeneous, with variation between 195 bp and 345 bp, and further evaluation of the recovered fragments confirmed that the products are likely to be xylanase gene fragments based on homology to known genes. Thus, in accordance with the present invention there is provided a method for recovering xylanase DNA from soil, comprising the steps of:

(a) treating a soil sample to render DNA in the soil accessible for hybridization with oligonucleotide primers;

(b) combining the treated soil sample with first and second primers in an amplification reaction mixture, said first and second primers hybridizing with conserved regions of the sense and antisense strands respectively of a gene encoding a xylanase and flanking a region of interest in the gene;

(c) thermally cycling the amplification reaction mixture through a plurality of cycles each including at least a denaturation phase and a primer extension phase to produce multiple copies of the region on interest flanked by the primers; and (d) recovering the copies of the region of interest from the amplification reaction mixture.

The soil sample employed in the present invention may be any type of soil that includes a mixture of mineral and organic materials. In the initial step of the method of the invention, a soil sample is treated to render the DNA accessible to the primers and enzymes employed in the amplification reaction. For example, DNA can be rendered accessible by a direct lysis procedure in which soil is treated with lysozyme, followed by Proteinase K, and then extracted with an organic solvent. DNA is precipitated from the aqueous phase and then further purified by chromatography. Incorporation of soil DNA into a phage library can also be performed, and such a library is a form of a treated soil sample within the scope of the present invention.

The treated soil sample is combined with two primers for PCR amplification in an amplification reaction mixture. The basic requirements for PCR amplification are well known, for example from U.S. Pat. No. 4,683,202 of Mullis, which is incorporated herein by reference and will not be described in detail. In general, however, the amplification reaction will include a thermostable polymerase enzyme such as Taq or Ultratherm™ polymerase and all four types of nucleotide triphosphates (A, C, G and T) in a buffer suitable for primer extension reactions.

The primers employed in the method of the invention can be any pair of primers which bind to conserved regions on complementary strands of a cellulase/xylanase gene and which flank a region of interest because of suspected structural diversity. FIG. 1 shows the location of the primers used by Bergquist et al. to amplify xylanase gene fragments from hot spring waters, which could be used to amplify soil DNA, and a preferred set of primers which produce larger fragments. These preferred primers are degenerate primers having the sequences forward primer:

CGS GGS CAC ACS XTS XTS TGG [SEQ ID NO 1], and reverse primer:

GTT GTA GTC GTT GWX GXA SA [SEQ ID NO 2], where S indicates a C or G, W indicates an A or T, and X indicates an inosine.

The amplification reaction mixture containing the primers and the treated soil sample is subjected to a plurality of thermal cycles to produce amplified DNA fragments corresponding to the region flanked by the primers. After thermal cycling, the amplification products are separated on an electrophoresis gel. Agarose gels have been found to be sufficient for this purpose, although polyacrylamide gels could also be used. Other separation techniques, including capillary electrophoresis and the use of biotinylated primers to facilitate capture of the amplified materials on an (strept) avidin-coated support might also be employed to recover the amplified DNA from the reaction mixture.

Because of the diversity of DNAs in soil samples, the products produced in the amplification reaction are likely to include more than one species of xylanase gene fragment. Thus, the recovered DNA is suitably cloned in a host organism to produce multiple copies of each species individually. We have used Invitrogen "Original TA cloning kit" that utilizes 3' A overhangs on the PCR product for ligation for cloning the amplified fragment into PCRII. This plasmid was then introduced into *E. coli* INVαF' by conventional means. The specific plasmid and host organism are not critical, however, and other plasmids and hosts could be also be used.

Plasmids containing the cloned soil DNA are recovered from the host organisms and evaluated by sequencing, preferably using a modification of the Sanger et al method. Sequencing primers that are the same as or similar to the original amplification primers can be used to obtain the sequence of the region flanked by the amplification primers, as can primers that hybridize with portions of the plasmid. Sequencing can be carried out using labeled primers or dye-labeled chain-terminating nucleotide triphosphates. The sequences determined are compared to known sequences for xylanase genes, for example using the BLAST program, to confirm that cloned fragment is derived from a xylanase gene and to determine whether it has a previously uncharacterized sequence. Unique xylanase sequences are then further processed to obtain a complete gene of unique sequence for evaluation.

The process of obtaining a complete xylanase gene can be carried out in two ways. First, the recovered DNA, or selected portions thereof which contain unique base sequences can be used to select xylanase genes from a phage library containing soil DNA. While it will be understood that the specific techniques and reagents employed in construction of a library permit the exercise of a great many personal preferences, we constructed a library from soil DNA prepared by a modification of the method described by Holben et al., *Appl. Environ Microbiol.* 53: 703–711 (1988). In this process, soil samples are homogenized and the centrifuged at progressively greater g to isolate a bacterial pellet. The pellet is suspended in buffer, treated with Sarkosyl and then lysed with lysozyme. The lysed cells are treated with pronase followed by Sarkosyl. DNA is extracted from the bacterial lysate supernatant by a standard phenol/chloroform extraction and then precipitated by isopropanol. The DNA was further purified by centrifugation through Sephadex G-200 columns as follows.

The resulting soil DNA was partially digested (less than 20 minutes exposure to the enzyme) with 0.5 units of restriction endonuclease BstY I per ug of DNA and loaded on an 0.3% agarose gel from which 6 to 12 kilobase fragments were electroeluted. The ligation, packaging, and amplification protocols were followed as per Stratagene's Predigested ZAP Express BamHI/CIAP Vector Cloning Kit, and the Gigapack III Gold Packaging Extract. The ligation was carried out with a 1 to 5 molar ratio of vector to insert DNA.

The resulting library is then screened to identify members of the library containing xylanase genes using probes based upon the novel sequences found from the initial amplification of soil DNA. The probe sequence may be the full length polynucleotide produced by amplification of the soil DNA and cloning. Alternatively, the probe sequence may be a polynucleotide which includes one or more of the unique genetic variations detected in the amplified products, in an otherwise known xylanase gene fragment. Probes used in this step may have lengths in the range of from 20 to 1500 bases, preferably 100 to 1000 bases.

Once identified, phagemids containing the selected xylanase inserts can be recovered and evaluated. The xylanase insert can, for example, be sequenced using primer walking over the inset to confirm the presence of the desired variation, or may be expressed and the expressed enzyme evaluated to determine the properties of the enzyme encoded by the insert.

As an alternative to the use of probes to isolate naturally occurring enzymes which deviate from the standard xylanase sequences, constructed xylanase genes can be formed using techniques such as site-directed mutagenesis or PCR-directed domain shuffling (See Crameri et al., *Nature Biotechnology* 14: 315–319 (1996), to introduce one or more sequence variations corresponding to variations found in amplified soil sample DNA. General techniques for introducing defined variations into known sequences are well known in the art, and will not be repeated here.

Figure 2:
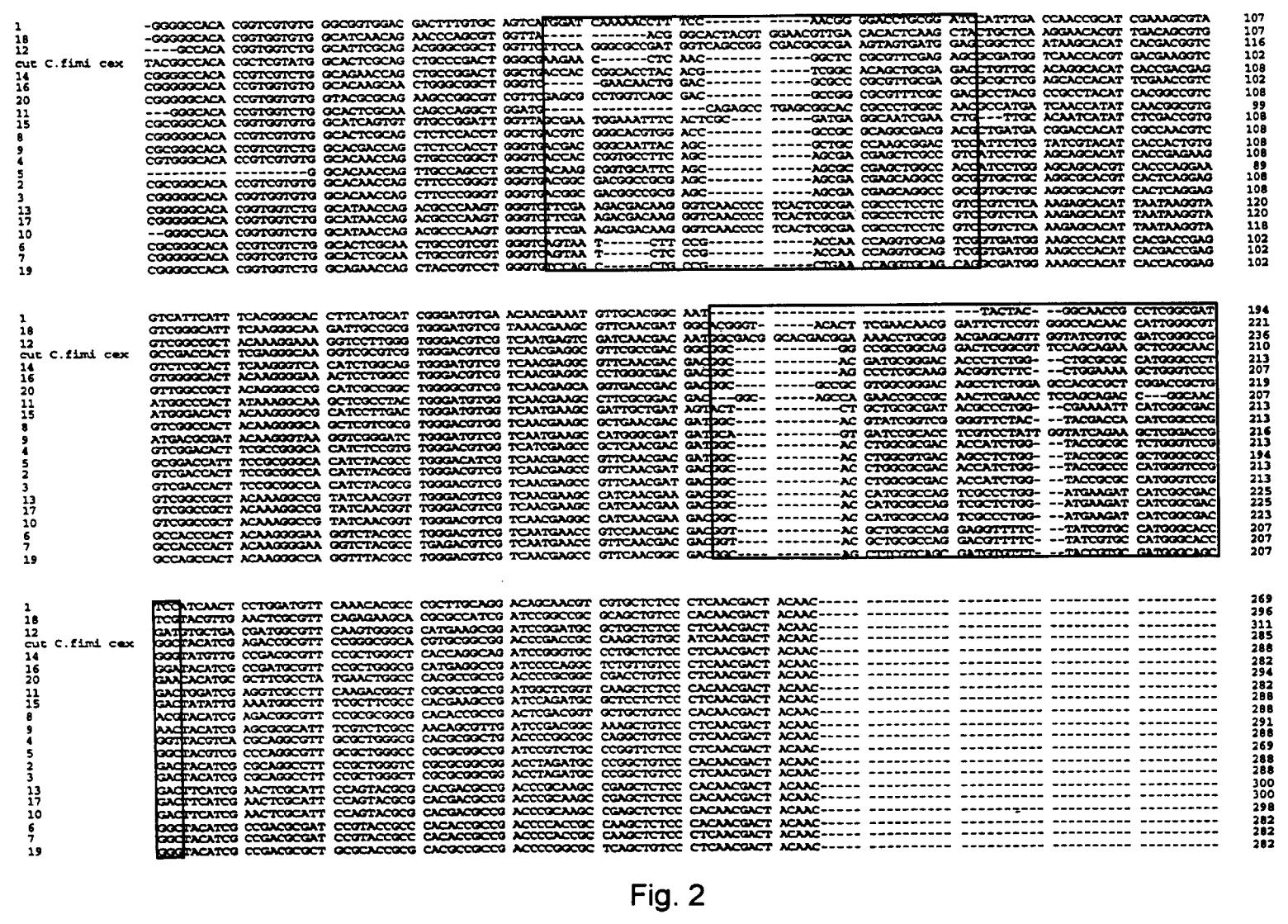

Using the method of the invention, the present inventors have isolated and sequenced a total of twenty different xylanase DNA fragments that do not correspond to previously known xylanases and one complete novel xylanase gene. The sequences of these fragments and gene are given Seq. ID Nos. 3–22. FIG. 2 shows a comparison of the fragment sequences with the corresponding region of the xylanase from *C. fimi* (Seq. ID No. 23), with boxes drawn around regions containing regions of significant variability. Polynucleotides including one or more of these variations, and particularly polynucleotides including the boxed regions, can be utilized in designing probes or recombinant genes as discussed above.

The invention will now be further described with reference to the following non-limiting examples.

EXAMPLE 1

DNA was extracted from a soil sample using the "direct lysis" method as described in Barns et al., *Proc. Natl. Acad. Sci.* 91: 1609–1613 (1994). The resulting extracted soil sample was combined with two degenerate primers targeting highly conserved regions of family F cellulases, namely:

5'-CG(CG) GG(CG) CAC AC(CG) XT(CG) XT(CG) TGG-3 [Seq ID No 1] and

5'-GTT GTA GTC GTT G(AT)X GXA (CG)A-3' [Seq ID No. 2]

where "X" indicates an incline. Incline was used to decrease the degeneracy of each primer. Patil, et al., *Nucleic Acid Res.* 18: 3080 (1990). These primers flank an active site of Family F cellulases such that variations in recovered sequences are likely to be significant to the function of the enzyme.

Amplification was performed on a MJResearch PTC-100 thermocycler as follows: 25–80 ng of template DNA, 0.50 ug of each primer, 50 uM of each dNTP, 1.5 mM of $MgCl_2$, 1× of 10×Taq buffer, and 5 U of Taq polymerase (buffer and polymerase from GibcoBRL), were mixed wish sterile distilled water to 50 ul. Following a "hotstart" of 94° C. for 3 min, cooling the mix in ice for 5 min, centrifuging, and maintaining at 80° C. while loading the polymerase, a "touchdown" protocol was utilized to overcome the Tm difference of the primers and to prevent spurious priming. Don, et al.,*Nucleic Acids Res.* 19: 4008 (1991); Roux, K. H., *BioTechniques* 16: 812–814 (1994). Thermocycling: denaturation, 94° C. for 50 sec; annealing, 65° C. for 1 min; extension, 72° C. for 1 min; and for the first 10 cycles, the annealing temperature was lowered 1° C. per cycle until 55° C. was reached. Then a subsequent 25 cycles were carried out with the annealing temperature at 55° C. A final extension for 10 min at 72° C. was carried out. PCR products were analyzed by electrophoresis through a 1.5% agarose gel with ethidium bromide staining.

DNA was extracted from agarose gel by the QIAGEN Qiaex protocol, or by the "freeze-thaw" method involving the steps of: excision of the DNA band from the gel, freezing at −80° C. for 20 min, thawing at 37° C. for 10 min, the addition of 10 ul of $H_2O$, centrifugation at 15000 rpm in a minifuge for 2 min, then removing and saving the liquid. The extracted DNA was reamplified using the same primers, separated on an agarose gel and then cloned into pCRII plasmid using the Invitrogen "Original TA cloning kit." The plasmids were transformed into Invitrogen's competent *E. coli* cells.

Selection of cells containing transformed plasmids was performed by growth on LB media containing ampicillin and X-gal. White colonies were selected, and after overnight growth, cloned plasmids were purified using. either QIAwell 8, or tip-20 modified alkaline lysis, and resin plasmid extraction and purification kits (from QIAGEN Inc.) and sequenced using an Applied Biosystems, Inc. PRISM Ready Reaction DyeDeoxy Terminator Cycle Sequencing Kit on an ABI 373 Stretch sequencer. Geneworks (by IntelliGenetics Inc.), Apple Mac version, was used for resolving sequence ambiguities, translation, and alignment construction. The determined DNA sequences were sent to the NCBI BLAST database located at, e-mail: blast@ncbi.nlm.nih.gov for the comparison of DNA sequences against protein databases.

Using this method, eight DNA fragments, denominated herein as Seq. ID. No. 3 through 10 were identified. Blast analysis confirmed the assignment of these fragments as derived from a xylanase gene, but did not produce an exact match for any of the fragments.

EXAMPLE 2

The experiment of example 1 was repeated except that different PCR reagents and conditions were used. In place of Taq polymerase, 1 U of Ultratherm™ from BIO/CAN was used, and processed at a lower annealing temperature to see if this would generate a more diverse set of fragments. The thermocycling program used was: 94° C. for 30 seconds; 45° C. for 1 minute; increase temperature 1° C. per 5 seconds to 72° C.; 72° C. for 45 seconds; repeat the previous steps 4 times, each time increasing the annealing temperature by 2° C.; carry out 10 cycles of 94° C. for 30 seconds, 53° C. for 1 minute, 72° C. for 45 seconds; then 94° C. for 30 seconds, 55° C. for 1 minute, increase temperature 1° C. per 5 seconds to 72° C. and 72° C. for 45 seconds; then 30 cycles of 94° C. for 30 seconds, 55° C. for minute, 72° C. for 45 seconds; and a final extension step of 72° C. for 10 minutes. This resulted in the recovery of an additional ten fragments denominated as Seq. ID Nos. 11 through 20 herein.

EXAMPLE 3

To prepare a phage library, soil DNA was first prepared by homogenizing a 50 g soil sample in a homogenization buffer containing 1.43 mM $K_2HPO_4$, 1.01 mM $MgSO_4.7\ H_2O$, 2.14 mM NaCl, 4.75 uM $Fe_2(SO_4)_3.7\ H_2O$, 14.8 uM $MnSO_4.4\ H_2O$ to which sodium ascorbate was added just before use to achieve a final concentration of 0.2 M. The homogenate was filtered through cheese cloth and the recovered solids suspended in 100 mL TE buffer to form a bacterial suspension. The suspension was brought to 1 M Nacl by addition of 25 mL of 5 M NaCl incubated at room temperature for 10 minutes and then collected by centrifugation. The pellet was resuspended in TS buffer (50 mM Tris, pH 8.0; 50 mM NaCl) transferred to a 50 mL polycarbonate centrifuge tube and brought to a concentration of 0.1% Sarkosyl by addition of 50 uL of 20% Sarkosyl. This mixture was incubated at room temperature for 10 minutes, after which the bacteria were collected by centrifugation. The bacterial pellet was drained and suspended in 35 m: of Tris-sucrose-EDTA which contains 0.75 M sucrose, 50 nM Tris (pH 8.0) and 10 mM EDTA. Lysozyme was added to a final concentration of 5 mg/ml and the samples were incubated at 37° C. for 60 minutes. A pronase solution in TS buffer that had been predigested by incubation for 30 minutes at 37° C. was added to the bacteria-lysozyme mixture, mixed by vortexing, and then incubated at 37° C. for 60 minutes. The temperature was then raised to 65° C. and 0.25 ml 20% Sarkosyl was added and incubated for 10 minutes. DNA was extracted from the supernatant of the resulting bacterial lysate by a standard phenol/chloroform extraction. The DNA was then precipitated by isopropanol. The DNA was further purified by centrifugation through Sephadex G-200 columns as follows.

2 grams of Sephadex G-200 (Pharmacia Biotech) were washed 5 times with 75 ml TE Buffer pH 8.0 (10 mM Tris-HCl, 1 mM EDTA). Each time, the mixture was allowed to settle and excess TE drawn off before adding more TE. Then the Sephadex suspension was autoclaved. Excess TE was drawn off and the suspension brought to the original volume with high salt TE buffer pH 8.0 (10 mM Tris-HCl, 1 mM EDTA, 0.1M NaCl), shaken and allowed to settle. Excess TE was drawn off and the suspension was again brought to the original volume with high salt TE buffer, and shaken again. A 5 ml syringe was packed with sterile fiberglass to the 1 cc mark, and Sephadex added. This column was then spun in a swing-bucket centrifuge for 10 minutes at 1000×g in a sterile test tube, 500 ul of the high-salt TE was added, and the column was spun again for 10 minutes at 1000×g. The column was then transferred to a new test tube, the DNA added to the column, and spun for 10 minutes at 1000×g. For three more times, 500 ul of the high-salt TE was added and the column spun for 10 minutes at 1000×g. A final dry spin for 10 minutes at 1000×g was carried out. The DNA was then precipitated with 1/10 volume of 3M Sodium Acetate and two volumes of 95% Ethanol. The suspension was held over night at 4° C. This was then centrifuged for 20 minutes in a minifuge at 4° C., the supernatant was removed and replaced with 70% Ethanol and re-centrfuged. The supernatant was removed and the pellet was dried, and dissolved in TE (not high-salt).

The resulting soil DNA preparation was partially digested (less than 20 minutes exposure to the enzyme) with 0.5 Units of BstYI per ug of DNA and 6 to 12 kilobase fragments were electroeluted from 0.3% agarose gel. The ligation, packaging, and amplification protocols were followed as per Stratagene's Predigested ZAP Express BamHI/CIAP Vector Cloning Kit, and the Gigapack III Gold Packaging Extract. The ligation was carried out with a 1 to 5 molar ratio of vector to insert DNA.

Although probes having sequences derived from any of Seq ID Nos. 3 to 20 could have been used to screen the library, we chose to prepare additional probes by PCR amplification of the library stock. 5 ul of a $1.1 \times 10^5$ pfu/ul library stock, 50 uM final concentration of each dNTP, 0.5 uM final concentration of each degenerate primer (Seq. ID Nos. 1 and 2), 1.5 mM final concentration of $MgCl_2$, 10% DMSO, 1× of 10×Ultratherm buffer, 1 U of Ultratherm polymerase (buffer and polymerase from BIO/CAN Scientific, Ontario, Canada), and sterile, distilled water were mixed. Thermocycling: 94° C. for 50 seconds; 65° C. for 1 minute; 72° C. for 1 minute; and for the first 10 cycles, the annealing temperature was lowered 1° C. per cycle until 55° C. was reached. A subsequent 35 cycles were carried out with the annealing temperature at 55° C., then a final extension for 10 minutes at 72° C. The Invitrogen "Original TA cloning kit" was used for cloning as in Example 1. Extra ATP was added to a final concentration of 1 mM. Plasmid DNA was extracted and purified. with QIAGEN's tip-20 kit. The probe was prepared by digesting the TA vector with insert, with EcoRI. The digested sample was electrophoresed through a 1.2% agarose gel with ethidium bromide staining. The band of interest was cut out of the gel and the DNA fragment purified using QIAGEN's QIAEX kit. This procedure led to the identification of two additional xylanase fragments, denominated herein as Seq. ID Nos. 21 and 22. The fragment was labeled using GibcoBRL's Random Primers DNA Labeling System with [$\alpha$-$^{32}$P]dCTP as per provided protocol.

EXAMPLE 4

Screening of the library was performed using the fragment with the sequence given by Seq. ID. No. 21 as a probe. The screening protocol supplied with Stratagene's Predigested ZAP Express BamHI/CIAP Vector Cloning Kit was followed. The post-hybridization washes were as follows: two washes in 0.5×SSC, 0.1% (w/v) SDS at 55° C.; followed by one 0.5×SSC, 0.1% (w/v) SDS wash at 60 C. Next, Stratagene's recommended in vivo excision protocol was followed to isolate E. coli colonies containing the pBK-CMV phagemid with insert DNA. Phagemid DNA with insert was extracted and purified with QIAGEN's tip-20 kit.

EXAMPLE 5

A xylanase gene contained in a phagemid from the library was sequenced by primer walking over the insert using degenerate amplification primers (Seq. ID Nos. 1 and 2) as initial extension primers. Then, subsequent extension primers were constructed by looking at the previously-generated sequence data. The sequence of the xylanase gene and putative amino acid sequence of the encoded-xylanase are set forth herein as Seq. ID No. 24 and Seq. ID No. 25, respectively.

What is claimed is:

1. A xylanase DNA fragment recovered from soil by the method comprising the steps of
   (a) treating a soil sample to render DNA in the soil accessible for hybridization with oligonucleotide primers;
   (b) combining the treated soil sample with first and second oligonucleotide primers in an amplification reaction mixture, said first oligonucleotide primer consisting essentially of the nucleotide sequence of SEQ ID NO: 1 and said second oligonucleotide primer consisting essentially of the nucleotide sequence of SEQ ID NO: 2;
   (c) thermally cycling the amplification reaction mixture through a plurality of cycles each including at least a denaturation phase and a primer extension phase to produce multiple copies of DNA flanked by the first and second oligonucleotide primers; and
   (d) recovering the xylanase DNA fragment comprising the nucleotide sequences of said first and second oligonucleotide primers from the amplification reaction mixture;

wherein said DNA fragment is a portion of a gene that encodes a xylanase, and is 195 bp to 345 bp in size.

2. A xylanase DNA fragment isolated by the method comprising the steps of
   (a) combining a treated soil sample in which soil DNA is rendered accessible for hybridization with a polynucleotide probe consisting essentially of a nucleotide sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22; and
   (b) isolating from the treated soil sample a DNA fragment that specifically hybridizes with the probe a step (a) after two washes in 0.5×SSC, 0.1% (w/v) SDS at 55° C. and one wash in 0.5×SSC, 0.1% (w/v) SDS at 60° C., and that does not comprise SEQ ID NO: 23;

wherein said DNA fragment is a portion of a gene that encodes a xylanase.

3. The xylanase DNA fragment of claim 2, wherein the treated soil sample is a phage library prepared from soil sample.

4. An isolated xylanase polynucleotide comprising:
   (a) a nucleotide sequence that encodes a polypeptide that is encoded by the nucleotide sequence set forth in Seq. ID No. 24; and
   (b) the complement of the nucleotide sequence of (a).

5. An isolated nucleic molecule comprising a nucleotide sequence that hybridizes to the nucleotide sequence of SEQ ID NO: 24 after two washes in 0.5×SSC, 0.1% (w/v) SDS at 55° C. and one wash in 0.5×SSC, 0.1% (w/v) SDS at 60° C., and that encodes a naturally occurring xylanase that does not comprise the *C. fimi* xylanase sequence of SEQ ID NO: 23.

6. An isolated nucleic acid molecule comprising the nucleotide sequence of SEQ ID NO: 24.

7. A recombinant vector comprising the xylanase DNA fragment of claim 1 or 2.

8. A recombinant vector comprising the xylanase polynucleotide of claim 4.

9. A recombinant vector comprising the nucleic acid molecule of claim 5 or 6.

10. A genetically engineered host cell containing the xylanase DNA fragment of claim 1 or 2, and thereof.

11. A genetically engineered host cell containing the xylanase polynucleotide of claim 4.

12. A genetically engineered host cell containing the nucleic acid molecule of claim 5 or 6.

13. A recombinant *C. fimi* xylanase polynucleotide comprising a modified naturally occurring *C. fimi* xylanase polynucleotide sequence, wherein said naturally occurring *C. fimi* xylanase polynucleotide sequence is characterized by the presence of the nucleotide sequence of SEQ ID NO: 23, and wherein said naturally occurring *C. fimi* xylanase polynucleotide sequence is modified by replacing the nucleotide sequence of SEQ ID NO: 23 with a second nucleotide sequence consisting essentially of a nucleotide sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22.

* * * * *